United States Patent [19]

Frazier

[11] 4,041,550
[45] Aug. 16, 1977

[54] ARTIFICIAL PATELLA AND METHOD OF REPAIRING A NATURAL PATELLA

[76] Inventor: Calvin H. Frazier, 1808 Verdugo Blvd., Glendale, Calif. 91208

[21] Appl. No.: 710,360

[22] Filed: July 30, 1976

[51] Int. Cl.² ............................................. A61F 1/24
[52] U.S. Cl. .................................... 3/1.91; 128/92 C
[58] Field of Search ........................... 3/1, 1.9–1.911; 128/92 C, 92 D

[56] References Cited
U.S. PATENT DOCUMENTS

| | | | |
|---|---|---|---|
| 3,878,566 | 4/1975 | Bechtol | 3/1.91 |
| 3,927,423 | 12/1975 | Swanson | 3/1.91 |

FOREIGN PATENT DOCUMENTS 2,247,176  3/1974  Germany ........................ 128/92 D

*Primary Examiner*—Ronald L. Frinks
*Attorney, Agent, or Firm*—Robert C. Comstock

[57] ABSTRACT

An artificial patella for use in the human body in place of a natural patella which has been damaged beyond repair. The artificial patella comprises a rigid wafer-like member having a contour comparable to that of the natural patella. A plurality of spaced perforations extend through the artificial patella. The artificial patella is attached to the natural patellar tendon with a plurality of sutures which extend through the perforations and through the patellar tendon. The artificial patalla may then be attached to the patellar components of a patello-femoral prosthesis.

10 Claims, 5 Drawing Figures

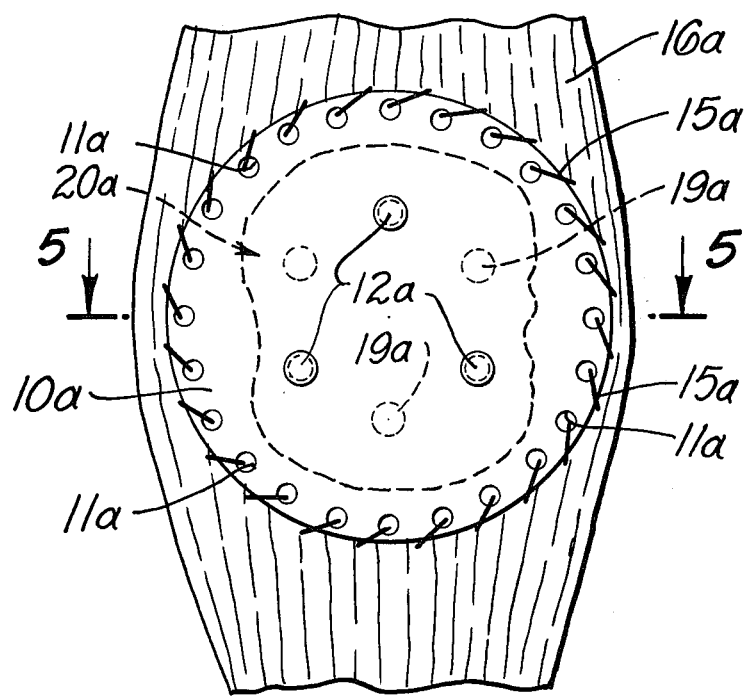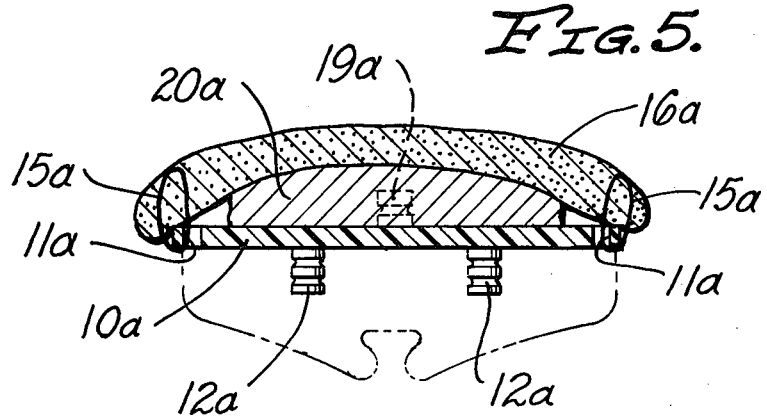

ARTIFICIAL PATELLA AND METHOD OF REPAIRING A NATURAL PATELLA

BACKGROUND OF THE INVENTION

1. Field of the invention

The invention relates to an artificial patella for use in the human body in place of a natural patella which has been destroyed or damaged beyond repair.

2. Description of the Prior Art

There are at the present time various types of patello-femoral prostheses for use in the knee joint. All of these are based on the premise that the natural patella is sufficiently intact to permit a patellar prosthesis to the attached to it.

There is at the present time no means of repairing or replacing the patello-femoral joint in cases where the natural patella is not sufficiently intact to support both itself and a patellar prosthesis which is in turn slidably connected to a femoral prosthesis.

SUMMARY OF THE INVENTION

The primary object of the present invention is to provide an artificial patella which is adapted to be implaced in the human body in place of the natural patella. The artificial patella is then attached to a patello-femoral prosthesis to complete the reconstruction of the knee joint.

This invention contemplates a wafer-like artificial patella having a plurality of openings extending through it which preferably extend across its entire surface area and which are adapted to receive sutures in order to attach the artificial patella to the natural patellar tendon. The artificial patella then functions in place of and in the same manner as the natural patella which it replaces. The artificial patella is attached to a patellar prosthesis which is in turn slidably connected to a femoral prosthesis either in the manner described herein or in other ways known to those skilled in the art such as that illustrated in Bechtol U.S. Pat. No. 3,878,566.

It is accordingly among the objects of the present invention to provide an artificial patella having all of the advantages and benefits of the structure set forth above and described in further detail hereinafter in this specification.

A further object of the invention is to provide an artificial patella which will function satisfactorily as a replacement for a damaged natural patella.

A more particular object of the invention is to provide such an artificial patella which can function satisfactorily in combination with a patello-femoral prosthesis.

The invention also comprises such other objects, advantages and capabilities as will later more fully appear and which are inherently possessed by the invention.

While there is shown in the accompanying drawings a preferred embodiment of the invention, it should be understood that the same is susceptible of modification and change without departing from the spirit of the invention.

DESCRIPTION OF THE DRAWINGS

FIG. 4 is a view similar to FIG. 2, showing a modified artificial patella in use with a damaged natural patella;

FIG. 5 is a sectional view taken on line 5—5 of FIG. 4.

DESCRIPTION OF THE PREFERRED EMBODIMENT

Figure 1:
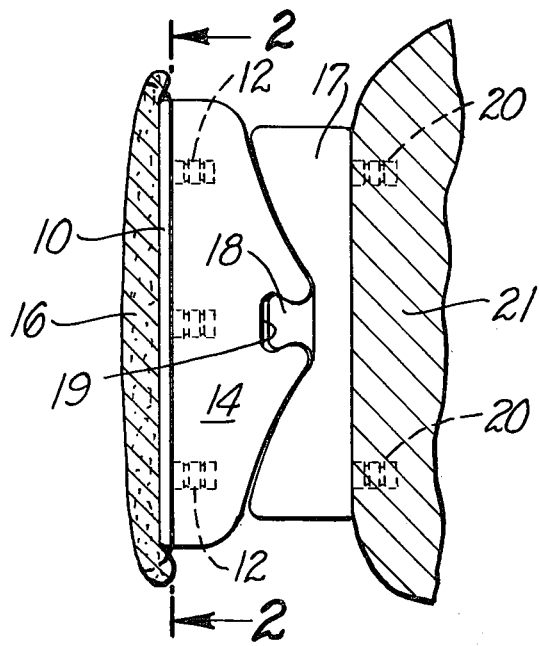
FIG. 1 is an end view of the artificial patella in use with a patello-femoral prosthesis.
Figure 3:
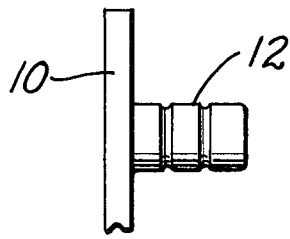
FIG. 3 is an enlarged partial elevational view of the artificial patella and one of the pegs.
Figure 2:
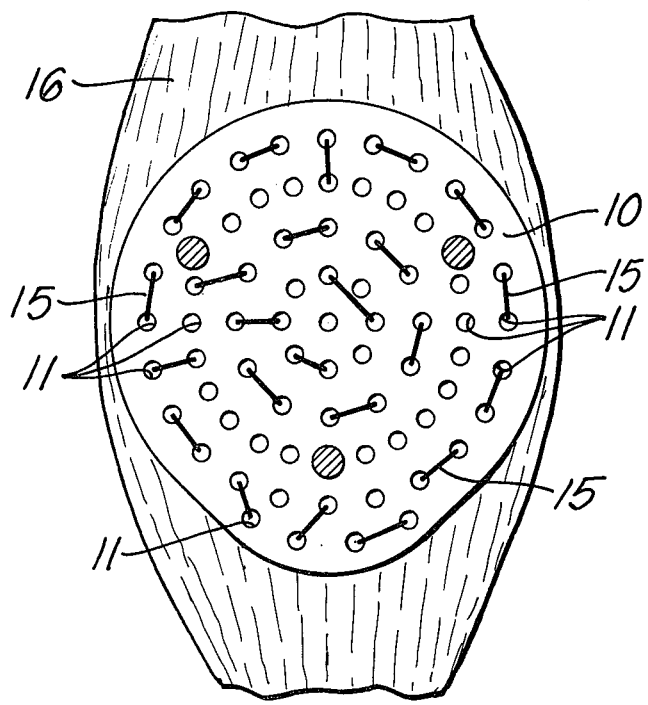
FIG. 2 is a section on line 2—2 rotated 90°.

A preferred embodiment which has been selected to illustrate the invention comprises an artificial patella 10, which is preferably in the form of a wafer formed of a substantially rigid material with a plurality of small circular openings 11 which extend completely through it and which are disposed across substantially its entire surface area.

The artificial patella 10 is preferably held in place on the human body by a plurality of sutures 15, which are laced through the openings 11 and through the adjacent patellar tendon 16 which extends across the outer surface of the natural patella. The sutures 15 form a lacework which holds the artificial patella 10 securely in place of the natural patella.

Extending inwardly from the inside surface of the artificial patella 10 are a plurality of pegs 12, which may be provided with spaced notches. The pegs 12 are adapted to extend into circular openings which extend inwardly into one face of a patellar prosthesis 14. The adjacent surfaces of the artificial patella 10 and the patellar prosthesis 14 are preferably secured together by conventional bone cement, which also extends into openings in the patellar prosthesis 14 to hold the pegs 12 in place.

The patellar prosthesis 14 is slidably connected to a femoral prosthesis 17 by means of a projection 18 carried by the femoral prosthesis 17 which slidably fits within an elongated groove 19 formed in the patellar prosthesis 14. The engagement between the prosthesis components may be of the type shown in the drawings herein in which the projection 18 is formed like a collar button in cross section and the groove is formed by a collar in cross section. With this type of engagement, undesirable lateral or radial movement of the prosthesis components with respect to each other is prevented. Separation of the components from each other is also prevented. The engagement between the prosthesis components may also be of the type shown and described in the Bechtol U.S. Pat. No. 3,878,566. The femoral prosthesis 17 is preferably secured to the femur 21 through the use of bone cement and pegs 20.

The groove 19 may be formed of somewhat resilient plastic material such as high density polyethylene, so that the projection 18 can be pressed into the groove like a "snap" bead.

Alternatively, the projection may be inserted by sliding movement into the top of the groove. The positions of the projection and groove may also be reversed, with the projection being on the patellar prosthesis and the groove being on the femoral prosthesis.

Instead of having circular openings 11 extending across the entire surface area of the artificial patella 10, it may be provided with a lesser number of openings such as one or more rows of openings extending around the periphery of the artificial patella. The number of openings and sutures used will vary with each patient and surgeon.

Instead of cementing the artificial patella 10 to the patellar prosthesis 14, these two members may be attached together by means of a press-in immovable "snap" connection, with the patellar prosthesis 14 having deformable openings for receiving projections carried by the artificial patella 10.

FIGS. 4 and 5 of the drawings show a modified artificial patella 10a which is adapted for use in a partial patellectomy application in which the natural patella has been either intentionally or inadvertently cut down in thickness and/or diameter. This can occur where the natural patella is damaged but not destroyed or where the natural patella is inadvertently cut down too much in thicknes in preparation for attachment to a patellar prosthesis. Whenever a situation arises in which the natural patella does not have sufficient thickness to permit it to be securely attached to a patellar prosthesis, the modified artificial patella 10a can be used.

The modified artificial patella 10a is constructed similar to the previously described artificial patella 10, except that the openings 11a need only be arranged around its periphery. The modified artificial patella 10a has one set of pegs 12a similar to the previously described pegs 12 on its inner side for attachment to a patellar prosthesis. It also has a second set of shorter pegs 19a on its outer side which are adapted to extend into complementary openings formed in the adjacent surface of the remaining natural patella 20a. The pegs 19a can be cut off to fit in the deepest openings which can feasibly be formed in the remaining natural patella 20a.

The artificial patella 10a is secured to the inner surface of the remaining natural patella 20a partly by means of the short pegs 19a which are held by bone cement. This attachment is enhanced and reinforced by sutures 15a which extend through the openings 11a around the periphery of the artificial patella 10a and through the natural patellar tendon 16a. The attachment is accordingly far more secure than could be obtained through the use of the short pegs 19a alone.

I claim

1. A method of repairing a natural patella which has been destroyed or damaged beyond normal repair comprising completely replacing or supplementing the remainder of said natural patella with an artificial patella, said artificial patella having a contour comparable to that of the undamaged natural patella, said artificial patella having a plurality of perforations, and suturing said artificial patella to the natural patellar tendon with a plurality of sutures extending through said perforations in said artificial patella and through the natural patellar tendon to securely attach said artificial patella in a position comparable to that of the natural patella, said artificial patella being adapted to function in a manner comparable to that of the natural patella.

2. The method described in claim 1, and fixedly securing said artificial patella to a patellar prosthesis.

3. The method described in claim 2, and slidably connecting said patellar prosthesis to a femoral prosthesis.

4. The method described in claim 3, in which said artificial patella is provided with a plurality of pegs, inserting said pegs into openings in said patellar prosthesis, and cementing said artificial patella to said patellar prosthesis with bone cement.

5. The method described in claim 4, in which said artificial patella is provided with second pegs on the opposite side from said first named pegs, inserting said second pegs into openings in the remaining portion of the natural patella, and cementing the artificial patella to the natural patella, so that said artificial patella is attached both to the patellar tendon and to the remaining portion of the natural patella.

6. An artificial patella for use in repairing a natural patella which has been completely destroyed or damaged beyond normal repair, said artificial patella being adapted to completely or substantially completely replace said natural patella, said artificial patella having a contour similar to that of the undamaged natural patella, said artificial patella hving a plurality of spaced perforations extending therethrough and having a generally continuous peripheral edge free of outwardly extending projections, and sutures extending through said perforations and adapted to extend through the natural patellar tendon to securely attach said artificial patella in a position comparable to that of the natural patella, said artificial patella being adapted to function in a manner comparable to that of the natural patella.

7. The structure described in claim 6, and a patellar prosthesis, and means securing said artificial patella to said patellar prosthesis.

8. The structure described in claim 6, and a patellofemoral prosthesis comprising a patellar prosthesis slidably connected to a femoral prosthesis, and means fixedly connecting said artificial patella to said patellar prosthesis.

9. The structure described in claim 8, said artificial patella having a plurality of pegs adapted to extend into openings in said patellar prosthesis and be held by bone cement.

10. The structure described in claim 9, said artificial patella having a second set of pegs on the opposite side thereof from said first named pegs, said second set of pegs adapted to extend into openings in the remaining portion of a natural patella, and be held by bone cement.

* * * * *